United States Patent [19]

Yoshida et al.

[11] Patent Number: 5,552,291
[45] Date of Patent: Sep. 3, 1996

[54] ANTI-HUMAN PULMONARY ADENOCARCINOMA SPECIFIC MONOCLONAL ANTIBODY

[75] Inventors: Hajime Yoshida, Kanagawa, Japan; Nobuo Hanai, Mercer Island, Wash.; Kenya Shitara, Tokyo, Japan

[73] Assignee: Kyowa, Hakko Kogyo Co., Ltd., Tokyo, Japan

[21] Appl. No.: 194,633

[22] Filed: Feb. 10, 1994

Related U.S. Application Data

[63] Continuation of Ser. No. 33,440, Mar. 18, 1993, abandoned, which is a continuation of Ser. No. 724,479, Jun. 28, 1991, abandoned, which is a continuation of Ser. No. 353,197, May 16, 1989, abandoned, which is a continuation-in-part of Ser. No. 262,042, Oct. 24, 1988, abandoned, which is a continuation of Ser. No. 916,275, Oct. 7, 1986, abandoned.

[30] Foreign Application Priority Data

Oct. 9, 1985 [JP] Japan ................................. 60-225327

[51] Int. Cl.$^6$ ........................ G01N 33/574; G01N 33/53
[52] U.S. Cl. ........................... 435/723; 435/7.92; 436/64; 436/513; 530/388.8; 530/388.85
[58] Field of Search .................................. 435/7.23, 7.92; 436/64, 513, 813; 530/388.8, 388.85

[56] References Cited

U.S. PATENT DOCUMENTS

| | | | |
|---|---|---|---|
| 4,818,682 | 4/1989 | Linnane | 435/7 |
| 4,892,934 | 1/1990 | Yoshida et al. | 530/388.8 |

FOREIGN PATENT DOCUMENTS

| | | |
|---|---|---|
| A-0156578 | of 1985 | European Pat. Off. . |
| A-0155571 | of 1985 | European Pat. Off. . |
| A-0151030 | of 1985 | European Pat. Off. . |
| 2142428 | 1/1985 | United Kingdom ............... 436/813 |

OTHER PUBLICATIONS

*Chemical Abstracts*, vol. 100, No. 11, 12 Mar. 1984, p. 405 Abstract No. 83935r, Varki et al "Antigens Associated with a Human Lung . . . ".

*The Carcinoembryonic Antigen Assay in Bronchogenic Carcinoma*, J. P. Concannon et al, pp. 184–192.

*Carcinoembryonic Antigen and Ferritin in Patients with Lung Cancer Before and During Therapy*, C. Gropp et al, pp. 2802–2808.

"Novel Fucolipids accumulating in Human Adenocarcinoma", The Journal of Biological Chemistry, 259, No. 16, 10511–10517 (1984).

"Location and Distribution of Difucoganglioside in Normal and Tumor Tissue Defined by its Monoclonal Antibody FH6", Cancer Research 45, 3711–3717, Aug. 1985.

"Quantitative and Qualitative Characterizatio of Human Cancer–Associated Serum–Fucoysl Type 2 Chain", Cancer Research, 46, 2619–2626, 1986 Kannagi et al.

"Characterization of Sialosylated Lewis$^x$ as a New Tumor-–Associated Antigen" Fukushima et al, Cancer Research, 44, 5279–5285, Nov. 1984.

Kohler et al., "Continuous cultures of fused cells secreting antibody of predefined specificity," Nature, v. 256, pp. 495–497 (Aug. 1975).

Hirota et al., "Sialosylated Lewis$^x$ in the Sera of Cancer Patients Detected by a Cell–binding Inhibition Assay", Cancer Research, v. 45, 1901–1905 (Apr. 1985).

DellVillano et al., "Immunoassay for carbohydrate antigenic determinant.," CAS:101,5475x (1984).

Primary Examiner—Toni R. Scheiner
Attorney, Agent, or Firm—Nixon & Vanderhye

[57] ABSTRACT

Monoclonal antibodies specific for human pulmonary adenocarcinoma recognizing sialylated glycoproteins or glycolipids as antigens but not reactive with normal human lung tissue. Hybridomas having the characteristics of cell line ALC-186 secrete such antibodies. Methods of diagnosing human pulmonary adenocarcinoma by immunoassay and immunohistochemical staining methods are described.

1 Claim, 6 Drawing Sheets

Fig. 2

INFLUENCE OF STAGE OF DISEASE UPON
THE RESULTS OF SERUM DIAGNOSIS OF PULMONARY
ADENOCARCINOMA USING MONOCLONAL ANTIBODY ALC-186

Fig. 3

(DILUTION)

Fig. 4

Reactivities of MoAbs by TLC-Immunostaining

Fig. 5

Analysis of KM-93 Antigen by TLC-Immunostaining

ANTI-HUMAN PULMONARY ADENOCARCINOMA SPECIFIC MONOCLONAL ANTIBODY

This is a continuation of application Ser. No. 08/033,440, filed Mar. 18, 1993 now abandoned, which is a continuation of Ser. No. 07/724,479 filed Jun. 28, 1991, now abandoned, which is a continuation of Ser. No. 07/353,197 filed May 16, 1989 now abandoned, which is a continuation-in-part of Ser. No. 07/262,042, filed Oct. 24, 1988, now abandoned which is a continuation of Ser. No. 06/916,275, filed Oct. 7, 1986, now abandoned.

BACKGROUND OF THE INVENTION

1. Field of the Invention

This invention relates to monoclonal antibodies characterized by their specificity to human lung cancer, in particular human pulmonary adenocarcinoma, and that the antigens (epitope) recognizable by them are sialylated glycoproteins or glycolipids, and to the use thereof in pathologic or serologic diagnosis or monitoring of pulmonary adenocarcinoma patients.

2. Description of the Prior Art

Methods of producing monoclonal antibodies capable of reacting specifically with tumors which comprise cultivating hybridomas obtained by fusing antibody-producing cells from an immunized animal with myeloma cells have recently been reported. It has been reported as well that monoclonal antibodies to human lung cancer can be obtained by such a technique [Cancer Res., 42, 150 (1982); Cancer Res., 42, 3187 (1982): J. Surgical Res., 30, 403 (1981); Transplantation Proceed., XIII (4), 1942 (1981); J. Immunol., 131 (1), 497 (1983); Abstracts of Papers, Japan Society of Immunology, P. 212 (Seishi Kyoizumi: Abstract No. 107) (1983)]. However, most of those monoclonal antibodies can react also with cancers other than lung cancer or with normal human cells; few are specific to lung cancer. Even those monoclonal antibodies that can be said to be relatively specific to lung cancer [J. Immunol., 131 (1), 497 (1983)] cannot distinguish such tissue types as squamous cell carcinoma and adenocarcinoma, although they can distinguish non-small cell from small cell lung cancer. No monoclonal antibodies applicable in serum diagnosis of lung cancer have not yet been reported.

A technique of serum diagnosis of digestive tract cancers using anti-human digestive tract cancer (stomach cancer, pancreas cancer, colon cancer) monoclonal antibodies has recently been reported. These monoclonal antibodies all recognize sialylated glycoproteins as serum antigens [J. Clin. Immunol, 2, 135 (1982); Federation Proc., 41, 898 (1982); Cancer Res., 42, 601 (1982); Hybridoma, 2, 110 (1983)]. On the other hand, monoclonal antibodies to lung cancer that recognize sialylated glycoproteins or glycolipids have not been reported at all.

Monoclonal antibodies reacting specifically with lung cancer, if available, would be useful in the diagnosis of lung cancer. While monoclonal antibodies to lung cancer are known, development of superior antibodies is desired. The present inventors have found that monoclonal antibodies produced by hybridomas between spleen cells of an antibody-producing mouse immunized with human pulmonary adenocarcinoma tissue membrane components, and mouse myeloma cells have particularly good reactivity with pulmonary adenocarcinoma and applicable in serum diagnosis of lung cancer and have now completed the present invention based on this finding.

SUMMARY OF THE INVENTION

The invention thus provides anti-human pulmonary adenocarcinoma-specific monoclonal antibodies obtained by fusing spleen cells of a mouse immunized with human pulmonary adenocarcinoma tissue membrane components with mouse myeloma cells, selecting from among the hybridomas obtained a hybridoma clone producing a monoclonal antibody having specificity to human pulmonary adenocarcinoma and cultivating the selected hybridoma in a medium or administering the hybridoma to a mouse to thereby cause hybridoma cell propagation in the ascitic fluid in the mouse, followed by separation from the culture or ascitic fluid, and the thus-separated hybridoma cells secreting antibodies capable of recognizing sialylated glycoproteins or glycolipids as antigens.

BRIEF DESCRIPTION OF THE DRAWINGS

In the accompanying drawings,

In FIG. 3, the symbols are used as follows: ● for treatment with 0.1 U/ml neuraminidase, △ for treatment with 0.1 U/ml α-L-fucosidase, □ for treatment with 0.25% trypsin, ■ for treatment with 10 U/ml protease, ○ for treatment with 50 mM $NaIO_4$, and X for no treatment.

FIG. 7 is a graph showing the reactivity of ALC-186 with fucogangliosides.

DETAILED DESCRIPTION OF INVENTION

The monoclonal antibodies according to the invention belong to the class IgM, specifically react with pulmonary adenocarcinoma cells and recognize sialylated glycoproteins or glycolipids as antigens.

As a typical example of the monoclonal antibodies according to the invention, there may be mentioned ALC-186 produced by the hybridoma cell line ALC-186 deposited at National Collection of Animal Cell Cultures on Aug. 29, 1985 under Budapest Treaty (NCACC 85082903).

In the following, a method of producing the monoclonal antibodies according to the invention is described in detail.

(1) Immunization of animal and preparation of antibody-producing cells

Mice of 3–10 weeks of age, preferably 8-week-old mice, are immunized with human pulmonary adenocarcinoma cells, tissues or membrane components to cause mice to prepare antibody-producing cells in the spleen, lymph node and peripheral blood. Mice that have immunological tolerance as a result of pretreatment with normal human lung cells should preferably be used as the mice to be immunized. The immunization is performed generally by administering human pulmonary adenocarcinoma cells ($10^6$ to $10^7$ cells per animal), human pulmonary adenocarcinoma tissues, or membrane components (membrane fragments) derived from such tissues (10–500 μg per animal) together with an appropriate adjuvant (e.g. Freund's complete adjuvant, or aluminum hydroxide gel plus pertussis vaccine) administered to the animals subcutaneously, intravenously or intraperitoneally. Thereafter, antigen administration is repeated 2–5 times at 1- to 2-week intervals. Three to seven days after each immunization, the blood is sampled from the eyeground venous plexus and the serum of each sample is tested as to whether it reacts with human pulmonary adenocarcinoma by the enzyme immunoassay technique given below [Enzyme-linked Immunosorbent Assay (ELISA), published by Igaku Shoin, Tokyo 1976], for instance.

Enzyme immunoassay technique:

The membrane components of normal or tumor cells or tissues (membrane fragment fraction containing 10–1,000 μg of proteins per ml) are distributed into wells of a 96-well plate for EIA (Flow Laboratories) (100–200 μl per well). After allowing the membrane components to stand overnight to two overnights at 4° C., each well is deprived of the supernatant and, then, washed well with deionized water or phosphate-buffered saline (PBS; 1.83 g of disodium phosphate, 0.21 g of monopotassium phosphate and 7.65 g of sodium chloride in each liter of distilled water, pH 7.2). Then, 1% BSA (bovine serum albumin)-PBS is distributed into the wells (100–200 μl per plate) and residual binding sites on the protein remaining on each well are blocked by allowing the culture to stand overnight to two overnights at 4° C. After discarding the BSA-PBS, the wells are washed well with deionized water or PBS. Samples (mouse sera, hybridoma culture supernatants, or roughly purified monoclonal antibodies; each as the first antibody) are diluted with BSA-PBS and the dilutions are distributed into the wells (100 μl per well), followed by overnight standing at 4° C. After washing the wells with one portion of deionized water and then with 6 portions of 2M NaCl solution, a 100-fold dilution of the rabbit anti-mouse immunoglobulin IgG-peroxidase conjugate (produced by DAKO and distributed by Kyowa Medex; used as the second antibody) is distributed into the wells (100 μl per well). The plate is then allowed to stand at room temperature for 2 hours.

After washing well with PBS, an ABTS substrate solution [prepared by dissolving 550 mg of 2,2'-azinobis (3-ethylbenzothiazoline-6-sulfonic acid) diammonium salt in 1 liter of 0.1M citrate buffer (pH 4.2) and adding, just prior to use, hydrogen peroxide to a concentration of 1 μl/ml] is applied and the color developed is measured in terms of the absorbance $OD_{415nm}$. Those mice that strongly react with the pulmonary adenocarcinoma cells, tissues or membrane components are used as human pulmonary adenocarcinoma-immunized mice, namely as sources of supply of antibody-producing cells for the hybridoma production.

When cells as they are used as the antigen in performing enzyme immunoassay, the target cells are cultivated on a Falcon 3072 plate, 0.25% glutaraldehyde-PBS is added and, after allowing to stand at room temperature for 1–2 hours, the plate is washed well with PBS. Then, 100–200 μl of 1% BSA-PBS is added and, after 2 hours of standing, the plate is washed well with deionized water or PBS and submitted to antibody titer determination, which is conducted in the same manner as the case where an ordinary antigen-coated plate is used.

For submitting to cell fusion, human pulmonary adenocarcinoma cells, tissues or membrane components are intraperitoneally administered to the immunized mice in a dose of 2 to $5 \times 10^6$ cells per animal or 20 to 400 μg per animal 3–4 days prior to the fusion treatment. The spleen is excised, cut into fragments in Eagle's minimal essential medium (MEM; Nissui Pharmaceutical) loosened up with a pair of forceps, and centrifuged at 1,200 rpm for 5 minutes. The supernatant is discarded, and the cells obtained as the sediment are deprived of erythrocytes by treatment with Tris-ammonium chloride buffer (pH 7.65) for 1–2 minutes, washed with three portions of MEM, and used as the spleen cells for fusion.

(2) Preparation of myeloma cells

A mouse-derived established myeloma cell line is used. Usable examples of such cell line are the 8-azaguanine resistant mouse (BALB/c-derived) myeloma cell lines P3-X63Ag8-U1 (P3-U1) [Current Topics in Microbiology and Immunology-1] [European J. Immunology, 6, 511–519 (1976)], SP2/0-Ag14 (SP-2) [Nature, 276, 269–270 (1978)], P3-X63-Ag8653 (653) [J. Immunology, 123, 1548–1550 (1979)] and P3-X63-Ag8 (X63) [Nature, 256, 495–497 (1975)], all of which are commercially available. The passage of these cell lines is performed in 8-azaguanine medium [normal medium prepared by adding, to RPMI-1640 medium, glutamine (1.5 mM), 2-mercaptoethanol ($5 \times 10^5$M), gentamicin (10 μg/ml) and fetal calf serum (FCS; produced by CSL) (10%), with further supplementation with 8-azaguanine (15 μg/ml)]. The cell line selected for cell fusion should be transferred to normal medium 3–4 days before fusion to ensure the cell count of not less than $2 \times 10^7$ on the day of fusion.

(3) Cell fusion

The antibody-producing cells immunized in (1) and the myeloma cells obtained in (2) are washed well with MEM or PBS and mixed in a cell number ratio of antibody-producing cells: myeloma cells=5 to 10:1 and then subjected to centrifugation (1,200 rpm, 5 minutes). The supernatant is discarded and the cell sediment is loosened up. With stirring at 37° C., a mixture of 2 g of polyethylene glycol 1000 (PEG-1000), 2 ml of MEM and 0.7 ml of dimethyl sulfoxide is added in an amount of 0.2–1 ml per $10^3$ antibody-producing cells, and the whole volume is made 50 ml by several additions of 1–2 ml of MEM at 1- to 2-minute intervals. After centrifugation (900 rpm, 5 minutes), the supernatant is discarded and the cell sediment is loosened gently. To the cells is added 100 ml of normal medium (RPMI 1640 with 10% FCS). The cells are suspended in the medium by gentle drawing up into the discharging from a measuring pipette.

The suspension obtained is distributed, in 1-ml portions, into the wells of a 24-well incubation plate. Incubation is carried out in a 5% $CO_2$ incubator at 37° C. for 24 hours. HAT medium (normal medium supplemented with hypoxanthine ($10^{-4}$M), thymidine ($1.5 \times 10^{-5}$M) and aminopterine ($4 \times 10^{-7}$M) is added to the incubation plate (1 ml per well) and incubation is conducted for a further 24 hours. Thereafter, 1 ml of the culture supernatant is discarded and the same volume of fresh HAT medium is added instead at 24-hour intervals for 2 days. The incubation in the $CO_2$ incubator at 37° C. is continued for 10–14 days.

For those wells in which fused cells grown and forming colonies are found, 1 ml of the supernatant is discarded and the same volume of HT medium (HAT medium minus aminopterine) is added, followed by medium replacement with fresh portions of HT medium at 24-hour intervals for 2 days.

After 3–4 days of cultivation in HT medium, a portion of the culture supernatant is collected and assayed for antibody titer relative to human pulmonary adenocarcinoma by the above-mentioned enzyme immunoassay technique. Simultaneously, the reactivities with normal human cells or tissues and membrane components thereof, among others, are also determined by a similar method, and those wells for which selective reactivity with human pulmonary adenocarcinoma cells or tissues or membrane components thereof are selected. For the wells showing strong reactivity with human pulmonary adenocarcioma cells or tissues or membrane components thereof but no reactivity with normal human cells or tissues or membrane components thereof, among others, cloning is repeated twice by the limiting dilution technique. In this way, those clones for which high antibody titer values are stably obtainable relative to human pulmonary adenocarcinoma cells or tissues or membrane components thereof are selected as anti-human pulmonary adenocarcinoma monoclonal antibody-producing hybridoma cell lines.

(4) Preparation of monoclonal antibodies

Eight- to ten-week-old female BALB/c mice treated with pristane [intraperitoneally administered with 0.5 ml of 2,6,10,14-tetramethylpentadecane (pristane) and fed for 2-weeks] are intraperitoneally injected with the anti-human pulmonary adenocarcinoma monoclonal antibody-producing hybridoma cells obtained in procedure (3) above at a dose of $2-4 \times 10^6$ cells per animal. In 10–21 days, the hybridoma cells produce ascites carcinoma in the mice. The ascitic fluid is collected from such a mouse, centrifuged (3,000 rpm, 5 minutes) to remove solids, subjected to salting out with 50% ammonium sulfate, dialyzed against PBS with NaCl added to 0.5M, and applied to a Sephacryl S300 (Pharmacia Fine Chemical) column (bed volume 750 ml) at a flow rate of 15 ml/hr. An IgM fraction is collected and used as a purified monoclonal antibody.

The isotype of the antibody is determined by Ouchterlony's method (double immunodiffusion) [Seibutsukagaku Jikkenho (Methods in Experimental Biochemistry), vol. 15, Introduction to Experimental Immunology, p. 74, Gakkai Shuppan Center, 1981].

The quantity of protein is estimated by the Folin method, followed by calculation based on the absorbance at 280 nm [1.4 ($OD_{280}$) approximately corresponds to 1 mg of immunoglobulin per ml].

The monoclonal antibodies thus obtained are evaluated for specificity characteristics based on the reactivities with (1) normal and tumor tissues and membrane components thereof derived from a variety of human organs obtained from a plurality of subjects, the reactivities with a variety of normal human or tumor cell lines and membrane components derived therefrom, (2) the reactivity with the hitherto known carcinoembryonic antigen (CEA) and (3) the reactivities with normal human-derived and patient-derived sera, among others, as determined by an appropriate assay technique, such as the enzyme immunoassay method, fluorescent antibody method, immunohistological evaluation method (ABC method), etc. Those monoclonal antibodies that react only with human pulmonary adenocarcinoma but do not exhibit reactivity in any other evaluation test are selected.

The thus-obtained monoclonal antibodies which react specifically with human pulmonary adenocarcinoma, are expected to be useful in diagnosis of lung cancer by serologic examination, histologic examination, imaging, etc., or in the treatment of lung cancer which comprises administering the antibodies as they are or in the form of the so-called immunotoxins, namely conjugates with anticancer agents or toxins, to cancer patients. It is further expected that these tumor-specific monoclonal antibodies might contribute, through the use of affinity columns in which they are used, to the purification of tumor-specific antigens, to the analysis of such antigens and further to the development of lung cancer vaccines.

(5) Serum diagnosis of lung cancer

The serum diagnosis is performed as follows:

A first antibody preparation (10–100 μg/ml) is distributed into the wells of a 96-well plate for EIA (50–200 μl per well). The plate is allowed to stand at 4° C. overnight to two overnights or at room temperature for 2–4 hours. After washing with PBS, 200 μl of BSA-PBS is added to each well, followed by further standing at 4° C. overnight or at room temperature for 2 hours. The plate is then washed well with PBS, and 50–100 μl of a 1- to 100-fold dilution of a serum sample is added to each well. After allowing the plate to stand at 4° C. overnight or at room temperature for 2 hours, the plate is washed well with PBS. Then, a biotin- or peroxidase-labeled second antibody (10–100 μg/μl) is added to the wells (50–100 μl per well) and the plate is further allowed to stand at 4° C. overnight or at room temperature for 2–4 hours. When a biotin-labeled antibody is used as the second antibody, the plate is washed well with PBS, avidin-biotin-peroxidase (10 μg/ml) is added to the wells (50–100 μl per well), and the plate is allowed to stand at room temperature for 30 minutes and then washed well with PBS. Then, an ABTS substrate solution is added, as the substrate solution, in an amount of 50–100 μl per well. After allowing the plate to stand at room temperature for 10–30 minutes, the reaction is terminated by adding 5% SDS solution in an amount of 50–100 μl per well. The $OD_{415}$ value is measured for each well and the quantity of the antigen in the serum sample is calculated based on the intensity of the color developed. By comparing the antigen levels in the sera of healthy humans with those in the sera of patients with lung cancer, a normal level range is defined. When the level in question exceeds such a predetermined range, the test for lung cancer is regarded as positive.

(6) Antigen analysis

When, in performing the above-mentioned enzyme immunoassay, immunohistochemical staining or serum diagnosis, the antigens (pulmonary adenocarcinoma membrane components, cultured lung cancer cell lines, lung cancer tissues) are pretreated with reagents such as enzymes (e.g. neuraminidase, protease) or periodic acid and then reacted with the monoclonal antibodies, the subsequent comparison for differences in reactivity with the monoclonal antibodies between the original antigens without such pretreatment and the antigens pretreated in the above manner can elucidate the chemical characteristics of the antigenic sites which the monoclonal antibodies recognize. Thus, if the antigenicity disappears upon treatment with neuraminidase, it is assumed that sialic acids are associated with the antigenic determinants. If the antigenicity disappears upon treatment with protease, it is assumed that proteins are associated with the antigenic determinants. If the antigenicity disappears upon periodic acid treatment, sugar chains are presumably associated with the antigenic determinants.

The following examples illustrate the invention in further detail.

EXAMPLE 1

(1) Preparation of antibody-producing cells

Normal human pulmonary tissue membrane components were administered intravenously to new-born BALB/c mice within 24 postnatal hours at a dose of 1 mg of proteins per animal. After the lapse of 8 weeks, the mice were intraperitoneally administered with human pulmonary adenocarcinoma membrane fragments (100 μg of proteins per animal) together with aluminum hydroxide gel (2 mg per animal) and killed pertussis vaccine ($1\times10^9$ per animal), followed by 3–5 immunizations with the same antigen at a dose of 100 μg per animal on the protein basis at 1- to 2-week intervals. From among these immunized mice, those mice whose antisera intensely reacted with human pulmonary adenocarcinoma cells or tissues or membrane fragments derived therefrom were selected, and spleen cells were prepared from such mice and submitted to cell fusion.

(2) Preparation of myeloma cells

The 8-azaguanine-resistant mouse myeloma cell line P3-U1 was cultivated in normal medium to thereby secure not less than $2\times10^7$ cells at the time of cell fusion, and submitted to cell fusion as a parent strain.

(3) Hybridoma production

The spleen cells and myeloma cells obtained in (1) and (2), respectively, were used in a ratio of 5:1 and subjected to fusion following the procedure mentioned hereinabove. After cultivation in HAT medium at 37° C. under 5% $CO_2$ for 14 days, fused cells were selected and, after change of the medium to HT medium, cultivation was continued. Based on the results of anti-human pulmonary adenocarcinoma antibody titer determination, active wells were selected and, after change of the medium to normal medium, cloning was repeated twice. The hybridoma cell line ALC-186 having no reactivity with normal human cells or tissues or other cancers but having specific reactivity with human pulmonary adenocarcinoma, as determined by various assay methods, was thus selected.

(4) Monoclonal antibody purification

Pristane-treated 8-week-old female BALB/c mice were intraperitoneally injected with the hybridoma cell line ALC-186 obtained in (3) at a dose of $4\times10^6$ cells per animal. In 10–21 days, the hybridoma produced ascites carcinoma. The ascitic fluid was collected from ascitic fluid-bearing mice (5–10 ml per animal), deprived of solids by centrifugation (3,000 rpm, 5 minutes), subjected to salting out with 50% ammonium sulfate, dialyzed against PBS supplemented with NaCl (0.5M), and applied to a Sephacryl S300 (Pharmacia Fine Chemicals) column (bed volume 750 ml) at a flow rate of 15 ml/hr. An IgM fraction was collected and used as purified antibody.

(5) Specificity of ALC-186

The results of testing of the thus-obtained antipulmonary adenocarcinoma-specific monoclonal antibody ALC-186 for reaction specificity expressed a fraction of positive reactions over the number of tests conducted, are summarized below in Table 1.

TABLE 1

|  |  | Antibody ALC-186 |
|---|---|---|
| Tissues | Pulmonary squamous cell carcinoma | 0/6 |
|  | Pulmonary adenocarcinoma | 4/6 |
|  | Normal lung | 0/6 |
|  | Normal tissues other than lung | 1/12* |
| Affinity analysis (ELISA) | CEA | — |

TABLE 1-continued

|  |  | Antibody ALC-186 |
|---|---|---|
| Cultured cell lines | Pulmonary squamous cell carcinoma | 0/1 |
|  | Pulmonary adenocarcinoma | 1/2 |
|  | Fetal lung | 0/1 |
|  | Cancers other than lung cancer | 2/5** |
|  | Normal | 0/1 |

*Weakly reacted with one of renal tissues.
**Weakly reacted with two cultured colon cancer cell lines.

EXAMPLE 2

Pulmonary adenocarcinoma tissues were immunohistochemically stained using the monoclonal antibody ALC-186 obtained in Example 1. Thus, paraffin-embedded block sections of pulmonary adenocarcinomas excised from 10 pulmonary adenocarcinoma patients were dewaxed in xylene, dehydrated through graded alcohols, and washed with distilled water. Endogenous peroxidase was blocked by immersion in 0.3% (wt/vol) hydrogen peroxide in absolute methanol for 30 minutes. The following steps were carried out using a Vectastain ABC kit (Vector Laboratories, Burlingame, Calif.) by the recommended procedure described in the text of Vector Laboratories. Briefly, after treatment with normal horse serum, purified monoclonal antibodies obtained in Example 1 were incubated on each section for 30 minutes and rinsed off with PBS. Biotinylated anti-mouse immunoglobulin horse antibody was incubated on each section for 30 minutes and washed with PBS. Then, avidin-biotinylated horseradish peroxidase was applied for 30 minutes and washed with PBS. Sections were incubated for 2 minutes in peroxidase substrate solution (mixture of 0.02% hydrogen peroxide and 0.1% diaminobenzidine tetrahydrochloride in 0.1M Tris buffer, pH 7.2). After washing with distilled water, the sections were counterstained with hematoxylin, dehydrated in ethanol, washed in xylene, and mounted. For 8 patients, cancer cells were stained intensely. The above results indicated that pathologic diagnosis of pulmonary adenocarcinoma is possible when ALC-186 is used for immunohistochemical staining.

EXAMPLE 3

Figure 1:
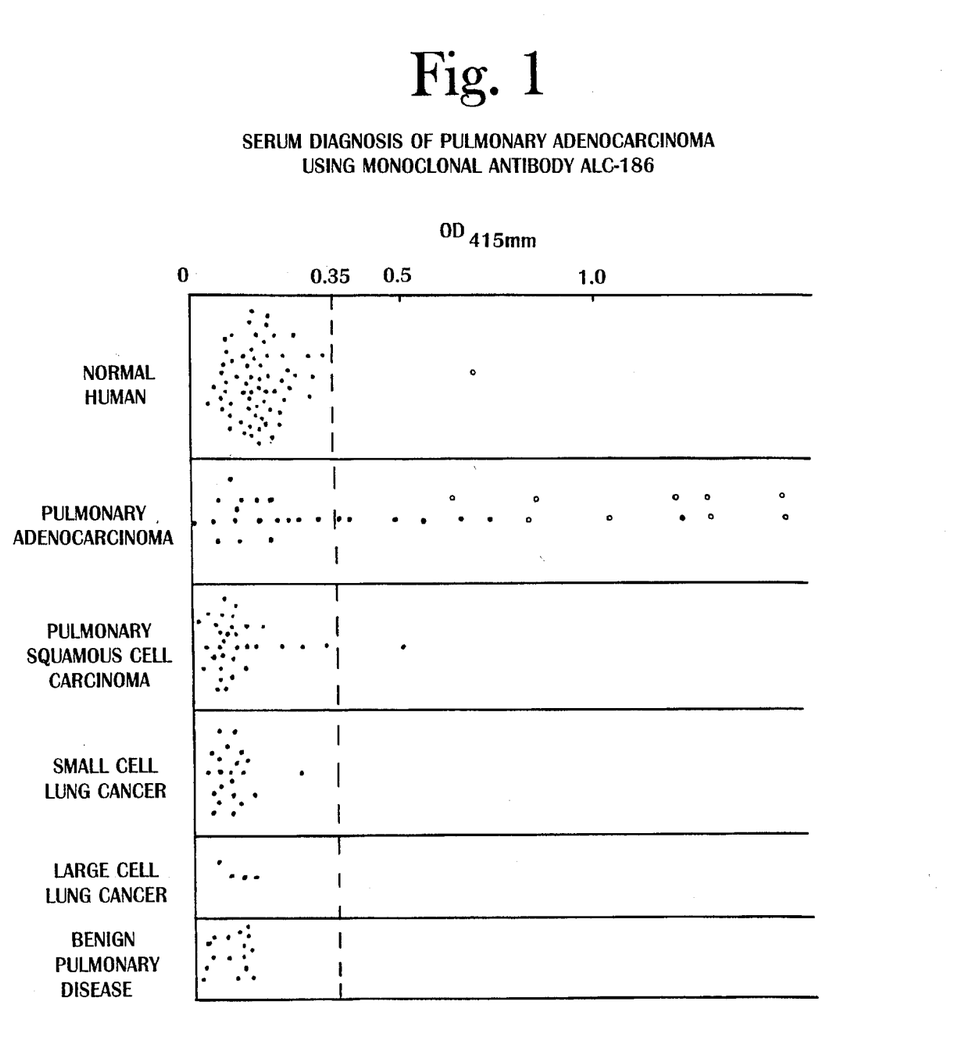
FIG. 1 is a scatter chart showing the results of serum diagnosis of pulmonary adenocarcinoma using the monoclonal antibody ALC-186.

A suspension of ALC-186 (10 μg/ml) was distributed in 50-μl portions into the wells of a 96-well plate for EIA (Flow Laboratories). After allowing it to stand overnight at 4° C., the plate was washed with PBS. Then, 1% BSA-PBS was added (200 μl per well). After overnight standing, the plate was washed well with PBS. To the plate were added 4-fold dilutions of normal human-derived sera (77 samples) or of lung cancer patient-derived sera (92 samples) in an amount of 40 μl per well. After overnight standing at 4° C. the plate was washed well with PBS. Then, biotin-labeled anti-lung cancer monoclonal antibody ALC-186 (10 μg/ml) was added as the second antibody (100 μl per well). The plate was allowed to stand overnight at 4° C. and, then, washed well with PBS. Avidin-biotin-peroxidase (product of Vector) (10 μg/ml) was distributed in 100-μl portions into the wells, and the plate was allowed to stand at room temperature for 1 hour and then washed with PBS. Thereafter, the ABTS substrate solution was added in an amount of 100 μl per well and the reaction was allowed to proceed at room temperature for 30 minutes and then terminated by adding 5% SDS (sodium dodecyl sulfate) soluton (100 μl per well). For each well, the color development was measured using an absorptionmeter ($OD_{415}$). As shown in FIG. 1, a positive result ($OD_{415}>0.35$) was obtained only for 1 out of the 77 serum samples from healthy subjects, whereas, for the serum samples from pulmonary adenocarcinoma patients, 16 out of 33 samples gave positive results ($OD_{415}>0.35$). This indicates that this serum diagnosis technique using the above antibody can identify pulmonary adenocarcinoma patients with a probability of 48%. For the serum samples from pulmonary squamous cell carcinoma patients, 1 out of 33 cases (3%) gave positive results ($OD_{415}>0.35$); for the serum samples from small cell lung cancer patients, none of 22 cases (0%); for the serum samples from large cell lung cancer patients, none out of 4 cases (0%); and, for the serum samples from benign pulmonary disease patients, none out of 16 cases (0%).

Figure 2:
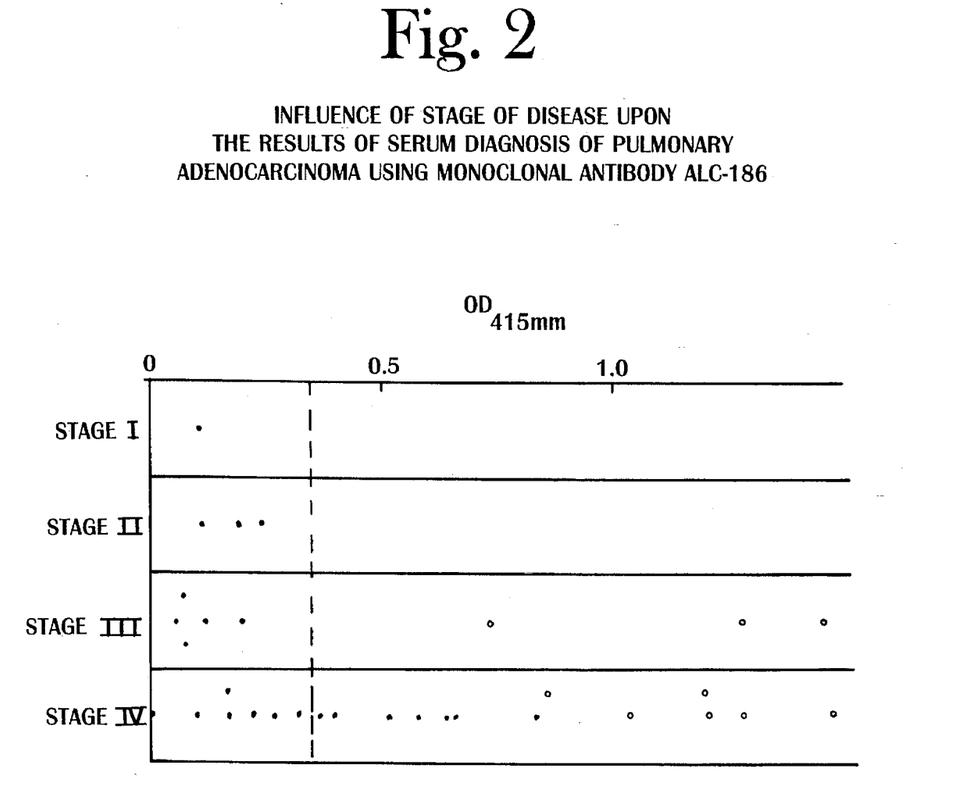
FIG. 2 is a scatter chart showing the influence of the stage of disease upon the results of serum diagnosis of pulmonary adenocarcinoma with the monoclonal antibody ALC-186.

Furthermore, as shown in FIG. 2, where the data obtained for the serum samples from pulmonary adenocarcinoma patients are plotted versus the stage of disease, positive results were obtained in 65% (13 out of 20 cases) of stage IV patients. This result shows that the serum diagnosis using the above antibody is effective in monitoring of pulmonary adenocarcinoma patients.

EXAMPLE 4

For analyzing the antigens which the monoclonal antibody ALC-186 recognizes, pulmonary adenocarcinoma tissue-derived membrane components were treated with the enzymes and reagent described below and then examined for the reactivity with ALC-186.

Enzymes and reagent

Trypsin (2.5% solution; Gibco)
0.25% in PBS
Neuraminidase (Boehringer Mannheim)
0.1 U/ml in 0.1M acetate buffer (pH 4.5)-3 mM $CaCl_2$
α-L-Fucosidase (Boehringer Mannheim)
0.1 U/ml in 0.1M phosphate buffer (pH 6.3)
Protease (Sigma)
10 U/ml in 0.1M phosphate buffer (pH 7.2)
$NaIO_4$ (Wako Pure Chemical)
50 mM in PBS Thus, the pulmonary adenocarcinoma tissue membrane components (100 μg of proteins per ml) were distributed, in 50-μl portions, into the wells of a plate for EIA (Linbro). After overnight standing at 4° C., the plate was washed three times with PBS. Then, 1% BSA-PBS was distributed into the wells (200 μl per well). The plate was allowed to stand at room temperature for 30 minutes to 2 hours and then washed three times with PBS. One of the above enzymes and reagent was distributed into the wells (50 μl per well) and the reaction was carried out at 37° C. for 1 hour. Then, the plate was washed five times with PBS and the monoclonal antibody ALC-186 (10 μg/ml) was distributed into the wells (50 μl per well), followed by allowing to stand at 4° C. overnight.

After washing five times with Tween 20 (Wako Pure Chemical)-PBS, peroxidase-labeled anti-mouse IgG (400-fold dilution) was added (50 μl per well), and the reaction was carried out at room temperature for 2 hours. The plate was washed five times with Tween 20-PBS, the ABTS substrate solution was added (100 μl), the reaction was conducted for 30 minutes, and the absorbance was measured at 415 nm.

Figure 3:
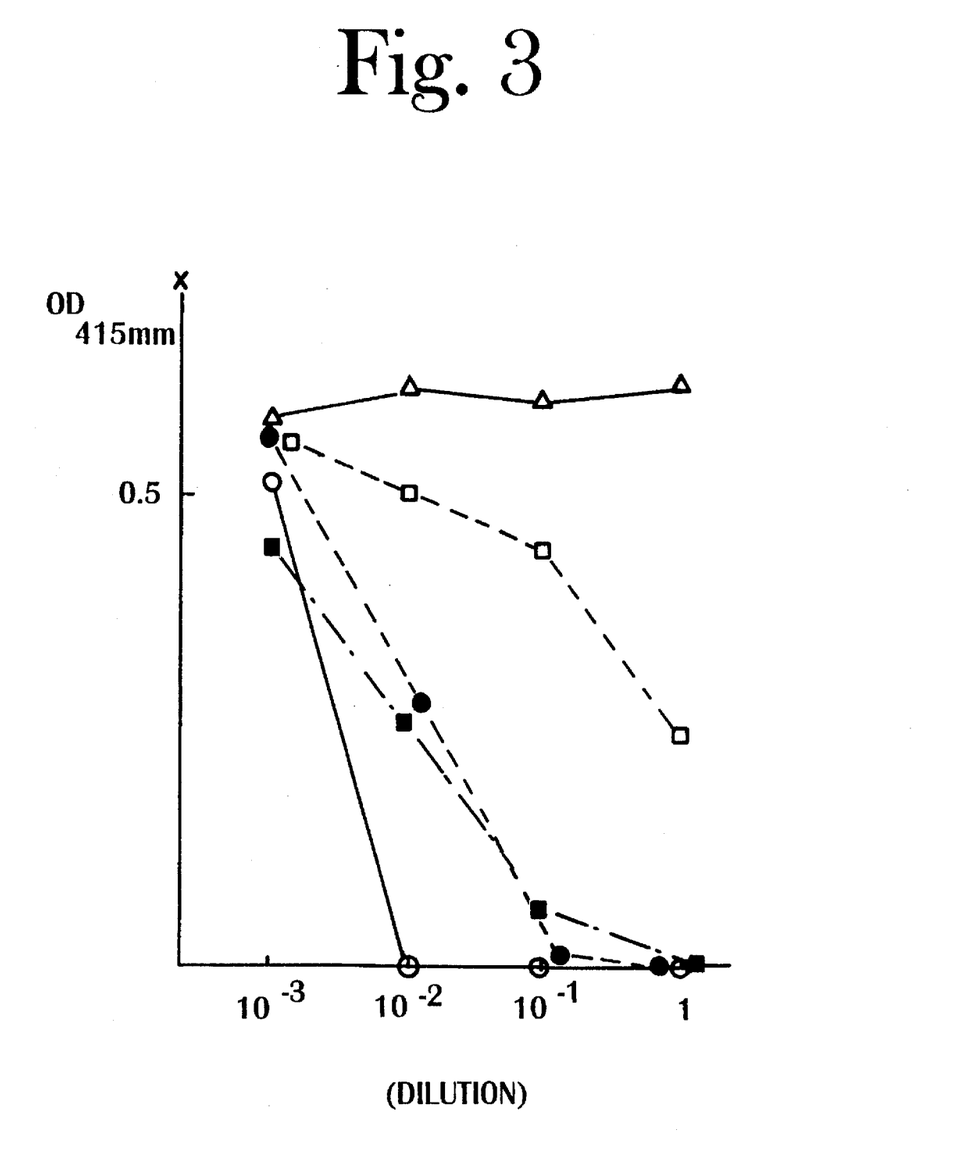
FIG. 3 is a graph showing the changes in reactivity of pulmonary adenocarcinoma tissue-derived membrane components with the monoclonal antibody ALC-186 upon treatment with various enzymes and a reagent.

As shown in FIG. 3, the antigenicity completely disappeared upon treatment with periodate ($NaIO_4$), neuraminidase or protease. Based on this, it was estimated that the monoclonal antibody ALC-186 recognizes sialylated glycoproteins.

EXAMPLE 5

Reactivities of the monoclonal antibodies ALC-186 and FH6 were measured by TLC-immunostaining.

Sialyl $Le^a$ and 6c fucoganglioside were prepared in accordance with the method as described in J. Biol. Chem., 257, 14365–14369 (1982) and Biochem. Biophys. Res. Commun., 113, 791–798 (1983), respectively. Kidney-derived monosialoganglioside was used as a sugar chain containing Sialyl $Le^x$ and Sialyl $Le^{x-i}$. TLC-immunostaining was carried out by the method as described in J. Biol. Chem., 257, 14865–14874 (1982).

The above gangliosides were applied to TLC plate (Baker) and development was carried out using a mixed solvent of chloroform, methanol and water (50:40:10) containing 0.02% of $CaCl_2$. After drying, the plate was blocked with 1% BSA-PBS,-ALC-186 (10 μg/ml) and FH6 (10 μg/ml) were applied thereto, and the reaction was carried out overnight at a room temperature.

After washing the plate, rabbit anti-mouse IgM (Miles) was applied thereto and allowed to react at a room temperature for 2 hours. Then, the plate was washed and $^{125}I$-labeled Protein A was applied thereto. The reaction was carried out at a room temperature for 2 hours. After washing the plate, $^{125}I$-binding spots were detected by autoradiography. The results are shown in FIG. 4.

Figure 4:
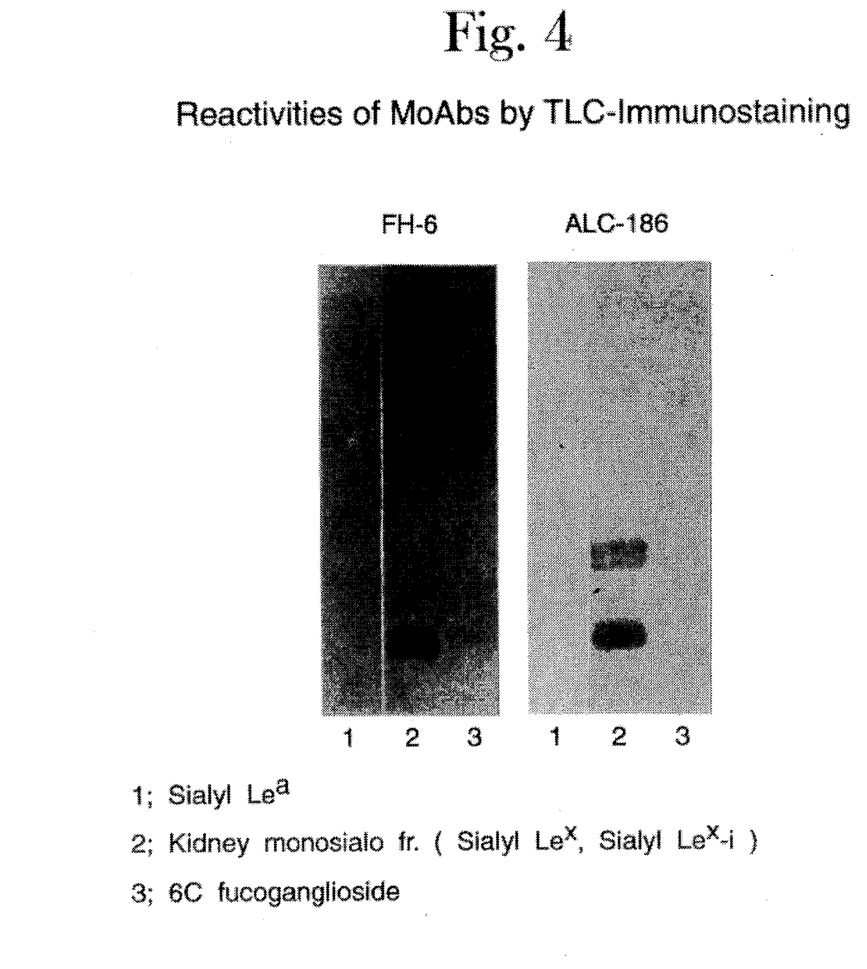
FIG. 4 is a photograph of a thin layer chromatography plate showing the reactivity of ALC-186 and FH6 with fucogangliosides.

It can be seen from the results shown in FIG. 4 that ALC-186 did not react with Sialyl $Le^a$ and 6c fucoganglioside, but reacted with Sialyl $Le^{x-i}$ and Sialyl $Le^x$, while FH6 reacted with Sialyl $Le^{x-i}$, but did not react with Sialyl $Le^x$.

Table 3 shows reactivities with fucoganglioside of ALC-186, FH6 and CSLEX 1. As shown in Table 1, it is found that (1) CSLEX 1 recognizes a Sialyl $Le^x$ structure since it strongly reacted with Sialyl $Le^x$ and Sialyl $Le^{x-i}$, (2) FH6 only reacted with Sialyl $Le^{x-i}$ and did not react with Sialyl $Le^x$, and (3) ALC-186 strongly reacted with Sialyl $Le^{x-i}$ and weakly reacted with Sialyl $Le^x$. Though the epitope which the three monolonal antibodies recognize is very similar, it can be assumed from differences in reactivity as described above that the three monoclonal antibodies each recognize the sugar chains different in length.

TABLE 2

| Ganglioside | | Reactivity | | |
|---|---|---|---|---|
| | | ALC-186 | FH6* | CSLEX1** |
| 6B ganglioside (Sialyl Le$^x$) | NeuAcα2→3Galβ1→4GlcNAcβ1→3Galβ1→1GlcNAcβ1→3Galβ1→1Glcβ1→1Cer<br>　　　　　　　　　　　　　　↑3<br>　　　　　　　　　　　　　Fucα1 | ++ | ++ | ++ |
| IV$^3$NeuAcIII$^3$FucnLc$_4$ (Sialyl Le$^x$) | NeuAcα2→3Galβ1→4GlcNAcβ1→3Galβ1→4Glcβ1→1Cer<br>　　　　　　　↑3<br>　　　　　Fucα1 | + | – | ++ |
| IV$^3$NeuAcIII$^4$FucnLc$_4$ (Sialyl Le$^a$) | NeuAcα2→3Galβ1→3GlcNAcβ1→3Galβ1→4Glcβ1→1Cer<br>　　　　　　　↑4<br>　　　　　Fucα1 | – | – | – |
| 6C fucoganglioside (VI$^6$NeuAcIII$^3$FucnLc$_6$) | NeuAcα2→6Galβ1→4GlcNAcβ1→3Galβ1→4GlcNAcβ1→3Galβ1→4Glcβ1→1Cer<br>　　　　　　　　　　　　　　↑3<br>　　　　　　　　　　　　Fucα1 | – | – | – |

Note:
++: strong reaction
+: weak reaction
–: no reaction
*: J. Biol. Chem, 259(16), 10511–10517, 1984
**: Cancer Res., 44, 5279–5285, 1984

EXAMPLE 6

1. Reactivity of ALC-186 with KatoIII-derived glycolipid

Reactivity of ALC-186 with stomach cancer cell, KatoIII-derived glycolipid was determined by TLC-immunostaining.

Neutral glycolipid, monosialoganglioside and polysialoganglioside, were prepared from KatoIII cells in accordance with the method as described in J. Biol. Chem., 263, 6296–6301 (1988). These glycolipids were spotted on the TLC silica gel plate (Baker) and development was carried out in the same manner as in Experimentation 1. A mixture of gangliosides, $GM_1$, $GM_2$, $GM_3$, $GD_{1a}$, $GD_{1b}$ and $GT_{ib}$, which were prepared in the method as described in J. Biol. Chem. 257., 14865–14874 (1987), was used as the standard. After development, the plate was blocked with 1% BSA-PBS, ALC-186 (10 μg/ml) was applied thereto and the reaction was carried out overnight at a room temperature. The plate was washed, biotinylated rabbit anti-mouse IgM (Vector) was applied thereto, and the reaction was carried out at a room temperature for 2 hours. Then, the plate was washed and peroxidase substrate (Bio Rad) solution was applied thereto to develop color. The spots of the standard gangliosides were detected with a resorcinol reagent (Merck). The results are shown in FIG. 5.

Figure 5:
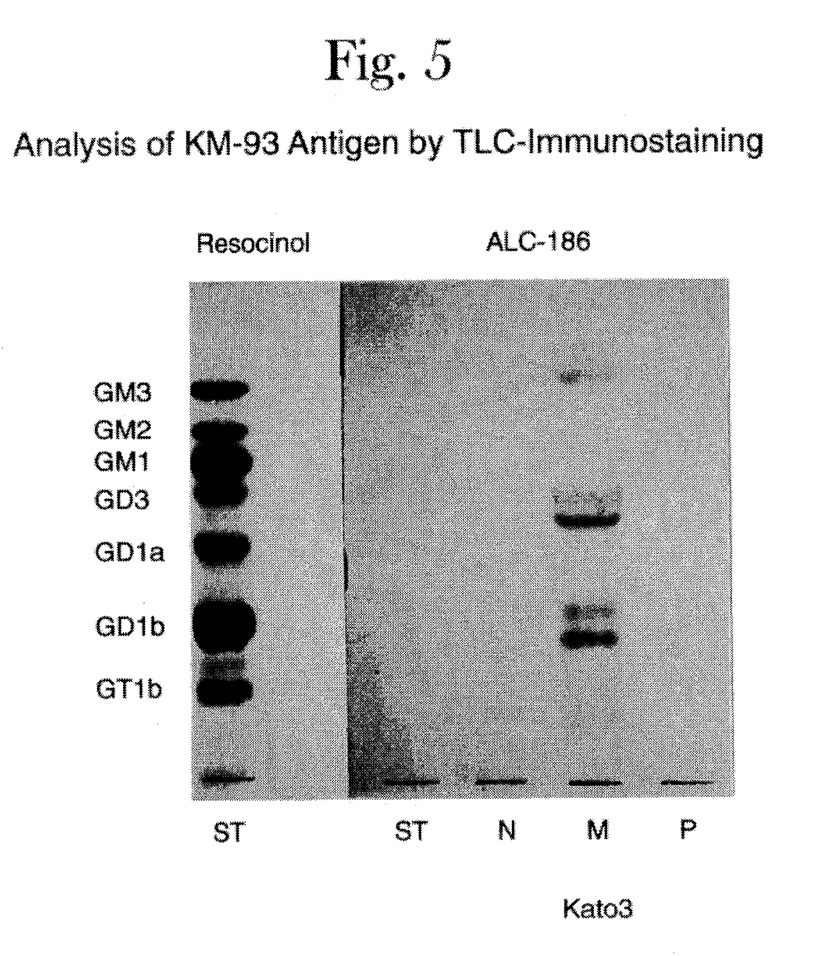
FIG. 5 is a photograph of a thin layer chromatography plate showing the reactivity ALC-186 with Kato III-derived glycolipid.

As shown in FIG. 5, it is assumed that, since ALC-186 reacted with only KatoIII-derived monoganglioside, there is the antigenic structure recognized by ALC-186 in monoganglioside derived from Kato III.

2. Reactivity of ALC-186 with Kato III-derived glycoprotien

The cell membrane fragments were prepared from KatoIII cells in accordance with the method as described in Cancer Research 46, 4438–4443 (1986) and the thus-obtained cell membrane fragments were used as KatoIII-derived glycoprotein. The fragments were solubilized by boiling at 92° to 1000° C. for 5 to 7 minutes in 0.0625M Tris-hydrochloride buffer (pH 6.8) containing 2% SDS, 10% glycerin and 0.001% bromophenyl blue. The resulting glycoprotein solution was subjected to polyacrylamide gel electrophoresis (SDS-PAGE) at 40 mA on 4 to 20% gradient gel (Tefco) in an electrophoretic buffer (pH 8.3) containing 0.025M Tris-hydroxyaminomethane, 0.192M glycine and 0.1% SDS according to the method of Leammli. After electrophoresis, gel was put on nitrocellulose membrane and glycoprotein fraction on the gel was transferred to the nitrocellulose membrane by Western blotting as described in J. Biochem. Biophys. Methods., 10, 203 (1984). Then, the nitrocellulose membrane was blocked with 1% BSA-PBS and ALC-186 (10 μg/ml) was applied thereon followed by allowing to react overnight at a room temperature. After washing the membrane, biotinylated rabbit anti-mouse IgM was applied thereon and was allowed to react at a room temperature for 2 hours. The membrane was washed, avidin-peroxidase was applied thereon and the reaction was carried out at a room temperature for 2 hours. After washing the membrane, peroxidase substrate was applied thereon to develop color. The results were shown in FIG. 6.

Figure 6:
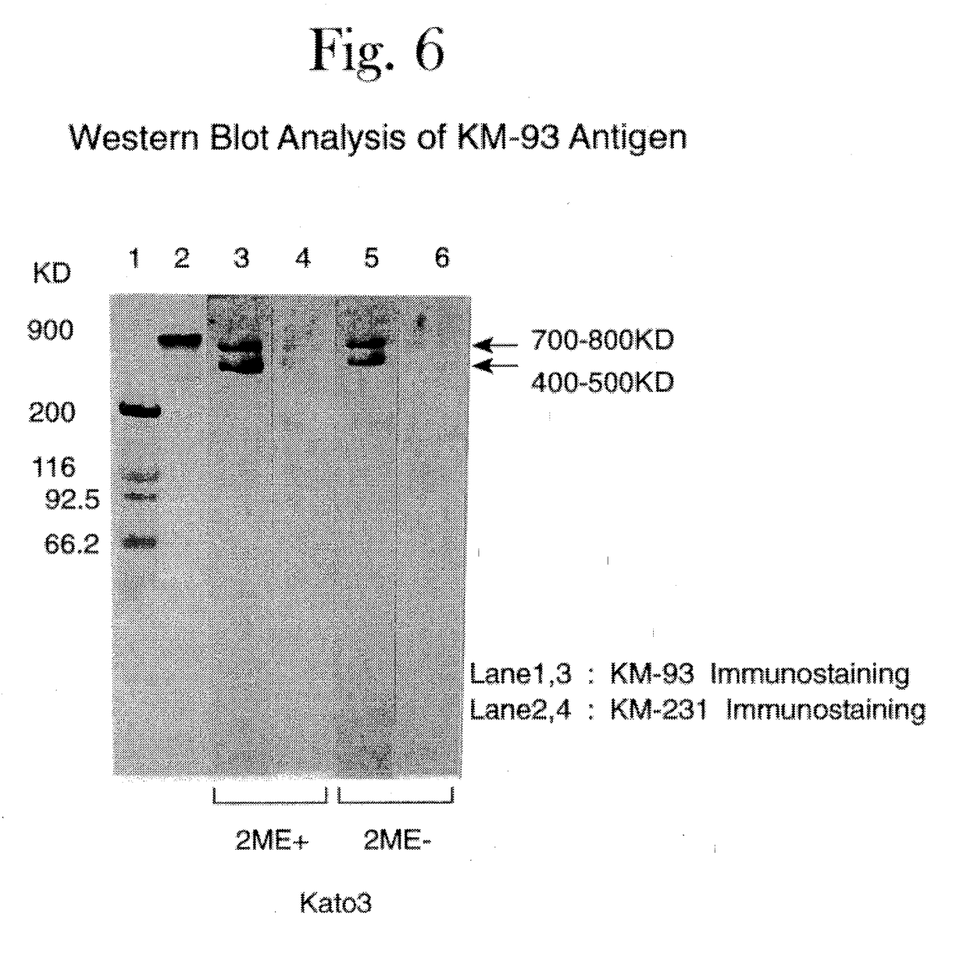
FIG. 6 is a plate showing the analysis of antigens on Kato III cell membrane recognized by ALC-186.

From the results as shown in FIG. 6, it can be seen that ALC-186 reacted with two bands of glycoprotein at a molecular weight of 700 to 800 kd and 400 to 500 kd. The two bands were independent of the presence of 2-mercaptoethanol. Accordingly, it is considered that there is the antigenic structure recognized by ALC-186 in KatoIII-derived glycoproteins having a molecular weight of 700 to 800 kd and 400 to 500 kd.

EXAMPLE 7

For analyzing the antigens which ALC-186 recognizes, pulmonary adenocarcinoma tissue-derived membrane components were treated with the enzymes and reagent described below and then examined for the reactivity with ALC-186.

Enzymes and reagent

Neuraminidase (Boehringer Mannheim)
0.1 U/ml in 0.1M acetate buffer (PH 4.5)-3mM $CaCl_2$ $NaIO_4$ (Wako Pure Chemical)
50 mM in PBS O-glycanase (Seikagaku Kogyo)
50 mM in citrate buffer (pH 4.5)

N-glycanase (Seikagaku Kogyo)
10 mM in phosphate buffer (pH 6.2)

Thus, the stomach cancer cell KatoIII membrane components (100 μg of proteins per ml) were distributed, in 50-μl portions, into the wells of a plate for EIA (Linbro). After overnight standing at 4° C., the plate was washed three times with PBS. Then, 1% BSA-PBS was distributed into the wells (200 μl per well). The plate was allowed to stand at room temperature for 30 minutes to 2 hours and then wahsed three times with PBS. One of the above enzymes and reagent was distributed into the wells (50 μl per well) and the reaction was carried out at 37° C. for 1 hour. Then, the plate was washed five times with PBS and ALC-186 (10 μg/ml) was distributed into the wells (50 μl per well), followed by allowing to stand at 4° C. overnight.

After washing five times with Tween 20 (Wako Pure Chemical)-PBS, peroxidase-labeled anti-mouse IgG (400-fold dilution) was added (50 μl per well), and the reaction was carried out at room temperature for 2 hours. The plate was washed five times with Tween 20-PBS, the ABTS substrate solution was added (100 μl), the reaction was conducted for 30 minutes, and the absorbance was measured at 415 nm.

TABLE 5

| Reagent/ enzymes | Conc. of Reagent/ enzymes | Inhibition raio (%) |
|---|---|---|
| $NaIO_4$ | 5 mM | 59.6 |
| " | 50 mM | 82.8 |
| Neuraminidase | 0.01 U/ml | 42.7 |
| " | 0.1 U/ml | 88.0 |
| O-glycanase | 0.1 U/ml | 61.5 |
| " | 1 U/ml | 38.4 |
| N-glycanase | 0.1 U/ml | 4.0 |
| " | 1 U/ml | 8.0 |

As shown in Table 3, it is found that the antigenicity was reduced upon treatment with O-glycanase, but did not change upon treatment with N-glycanase. Based on this, it was estimated that the sugar chain in the glycoprotein which ALC-186 recognizes is bound to protein via O-glycoside bond.

EXAMPLE 8

Reactive Specificity of the Monoclonal Antibody ALC-186

Reactivities of the monoclonal antibody ALC-186 to various fucogangliosides were measured by solid phase radioimmunoassay. Examples of fucogangliosides used were 6B-fucoganglioside (Sialyl $Le^{x-i}$), $IV^3NeuAcIII^3FucnLc_4$ (Sialyl $Le^x$), $IV^3NeuAcIII^4FucnLc_4$ (Sialyl $Le^a$) and 6c-fucoganglioside ($VI^6NeuAcIII^3FucnLc_6$).

6B-fucoganglioside was prepared from human colon cancer tissue in accordance with the method as described in J. Biol. Chem., 259, 10511–10517 (1984).

IV³NeuAcIII³FucnLc₄ (Sialyl Le$^x$) was prepared from human kidney tissue in accordance with the method as described in J. Biol. Chem., 2.51, 7517–7520 (1976). IV³NeuAcIII⁴FucnLc₄ (Sialyl Le$^a$) was prepared in accordance with the method as described in J. Biol. Chem., 257, 14365–14369 (1982). 6c-fucoganglioside (VI⁶NeuAcIII³FucnLc6) was prepared from human colon tissue in accordance with the method as described in Biochem. Biophys. Res. Commun., 113, 791–798 (1983).

Solid phase radioimmunoassay was carried out according to the method as described in Cancer Research 43, 4997–5005 (1983). Namely, 10 ng of each ganglioside was added to 50 μl of ethanol and the resulting solutions were adsorbed on each well of the 96-well plate (Costar) and were blocked with 1% BSA-PBS. After washing each well with PBS, 2-dilution series of ALC-186 with 1% BSA-PBS was added thereto with starting from an ALC-186 concentration of 10 μg/ml and the mixture was allowed to react for 2 hours. After washing each well with PBS, $^{125}$I-labeled Protein A (Pharmacia) was added thereto and the mixture was allowed to react for 2 hours. Each well was washed with PBS and counted with gamma counter. The results was shown in FIG. 7.

As shown FIG. 7, it was found that the monoclonal antibody ALC-186 strongly reacted with Sialyl Le$^{x-i}$ and weakly reacted with Sialyl Le$^x$, while no reaction was observed between the monoclonal antibody ALC-186 and Sialyl Le$^a$ and 6c fucoganglioside.

While the invention has been described in detail and with reference to specific embodiment thereof, it will be apparent to one skilled in the art that various changes and modifications can be made therein without departing from the spirit and scope thereof.

What is claimed is:

1. A method of screening for the presence of pulmonary adenocarcinoma in a patient, comprising:

contacting a serum sample from the patient with monoclonal antibody ALC-186, which is secreted by hybridoma cell line NCACC85082903; and detecting binding of the antibody to a pulmonary adenocarcinoma-associated antigen in the serum sample, wherein the presence of said binding is indicative of the presence of pulmonary adenocarcinoma.

* * * * *